United States Patent [19]

Nelson

[11] 3,983,163

[45] Sept. 28, 1976

[54] 5-OXA PHENYL- AND PHENOXY-SUBSTITUTED PROSTAGLANDIN β, ANALOGS

[75] Inventor: Norman A. Nelson, Galesburg, Mich.

[73] Assignee: The Upjohn Company, Kalamazoo, Mich.

[22] Filed: Nov. 18, 1974

[21] Appl. No.: 524,413

Related U.S. Application Data

[62] Division of Ser. No. 361,990, May 21, 1973, Pat. No. 3,864,387.

[52] U.S. Cl. .................. 260/473 A; 260/520 B
[51] Int. Cl.² .................................. C07C 69/76
[58] Field of Search.............. 260/473 A, 473 G, 520

[56] References Cited
FOREIGN PATENTS OR APPLICATIONS
2,165,184  7/1972  Germany ................ 260/473 A OTHER PUBLICATIONS
Derwent Abstract, 46347T, Apr. 7, 1972.

*Primary Examiner*—Paul J. Killos
*Attorney, Agent, or Firm*—Morris L. Nielsen

[57] ABSTRACT

5-Oxa phenyl- and phenoxy-substituted prostaglandin-$\beta_1$ type compounds and processes for making them. These compounds are useful for a variety of pharmacological purposes, including stimulation of epidermal proliferation and keratinization, and wound healing.

10 Claims, No Drawings

5-OXA PHENYL- AND PHENOXY-SUBSTITUTED PROSTAGLANDIN β, ANALOGS

CROSS REFERENCE TO RELATED APPLICATIONS

This application is a divisional of my co-pending application Ser. No. 361,990 filed May 21, 1973 now issued as U.S. Pat. No. 3,864,387.

BACKGROUND OF THE INVENTION

This invention relates to novel compositions of matter, to novel methods for producing those, and to novel chemical intermediates useful in those processes. Particularly, this invention relates to certain novel analogs of prostaglandins $E_1$, $F_{1\alpha}$, $F_{1\beta}$, $A_1$, and $B_1$ in which the C-5 methylene (—$CH_2$—) in the prostanoic acid structure is replaced by oxygen (—O—).

The essential material for this application, including the background of the invention, the disclosure of the invention, and the description of the preferred embodiments, including Preparations and Examples, is incorporated by reference from U.S. Pat. No. 3,864,387, columns 1–89 inclusive, under the provisions of M.P.E.P. 608.01(p).

I claim:

1. An optically active compound of the formula

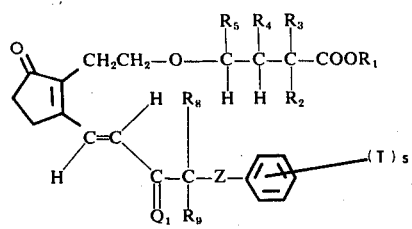

or a racemic compound of that formula and the mirror image thereof, wherein Z represents an oxa atom (—O—) or $C_jH_{2j}$ wherein $C_jH_{2j}$ is a valence bond or alkylene of 1 to 9 carbon atoms, inclusive, substituted with 0, 1, or 2 fluoro, with one to 6 carbon atoms, inclusive, between —$CR_8R_9$— and the ring; wherein T is alkyl of 1 to 4 carbon atoms, inclusive, fluoro, chloro, trifluoromethyl, or —$OR_{10}$, wherein $R_{10}$ is hydrogen or alkyl of 1 to 4 carbon atoms, inclusive, and $s$ is 0, 1, 2, or 3, with the proviso that not more than two T's are other than alkyl and when $s$ is 2 or 3 the T's are either the same or different; wherein $Q_1$ is

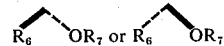

wherein $R_6$ and $R_7$ are hydrogen or alkyl of 1 to 4 carbon atoms, inclusive, being the same or different; wherein $R_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, or phenyl substituted with 1, 2, or 3 chloro or alkyl or one to 4 carbon atoms, inclusive; wherein when Z is oxa (—O—), $R_8$ and $R_9$ are hydrogen or alkyl or one to 4 carbon atoms, being the same or different, and, when Z is $C_jH_{2j}$, $R_8$ and $R_9$ are hydrogen, alkyl of 1 to 4 carbon atoms, inclusive, or fluoro, being the same or different, with the proviso that $R_9$ is fluoro only when $R_8$ is hydrogen or fluoro; wherein $R_3$ is hydrogen, alkyl of 1 to 4 carbon atoms, inclusive, or fluoro; wherein $R_2$ is hydrogen or fluoro, with the proviso that $R_2$ is fluoro only when $R_3$ is hydrogen or fluoro; and wherein $R_4$ and $R_5$ are hydrogen or alkyl of 1 to 4 carbon atoms, inclusive, being the same or different, with the proviso that no more than one of $R_3$, $R_4$, and $R_5$ is alkyl; including the lower alkanoates thereof, and the pharmacologically acceptables salts thereof when $R_1$ is hydrogen.

2. A compound according to claim 1 wherein $Q_1$ is

wherein $R_6$ and $R_7$ are hydrogen or alkyl of 1 to 4 carbon atoms, inclusive, being the same or different.

3. A compound according to claim 2 wherein $R_2$, $R_3$, $R_4$, and $R_5$ are hydrogen.

4. A compound according to claim 3 wherein $R_6$, $R_7$, $R_8$, and $R_9$ are either hydrogen or methyl, and one of $R_6$, $R_7$, $R_8$, and $R_9$ is methyl.

5. A compound according to claim 3 wherein $R_6$, $R_7$, $R_8$, and $R_9$ are hydrogen.

6. A compound according to claim 5 wherein Z is oxa (—O—).

7. A compound according to claim 5 wherein Z is methylene.

8. A compound according to claim 7 wherein $R_1$ is alkyl of 1 to 12 carbon atoms, inclusive.

9. 5-Oxa-17-phenyl-18,19,20-trinor-$PGB_1$, methyl ester, a compound according to claim 8.

10. A compound according to claim 7 wherein $R_1$ is hydrogen.

* * * * *

UNITED STATES PATENT OFFICE
CERTIFICATE OF CORRECTION

Patent No. 3,983,163          Dated September 28, 1976

Inventor(s) Norman A. Nelson

It is certified that error appears in the above-identified patent and that said Letters Patent are hereby corrected as shown below:

Column 1, line 1: "5-OXA PHENYL- AND PHENOXY-SUBSTITUTED PROSTAGLANDIN β, ANALOGS" should read, -- 5-OXA PHENYL- AND PHENOXY-SUBSTITUTED PROSTAGLANDIN $B_1$ ANALOGS --.

Title: (cover) should read -- 5-OXA PHENYL- AND PHENOXY-SUBSTITUTED PROSTAGLANDIN $B_1$ ANALOGS --.

Signed and Sealed this

First Day of March 1977

[SEAL]

Attest:

RUTH C. MASON
*Attesting Officer*

C. MARSHALL DANN
*Commissioner of Patents and Trademarks*